(12) United States Patent
Podolski et al.

(10) Patent No.: US 9,545,411 B2
(45) Date of Patent: Jan. 17, 2017

(54) METHODS AND COMPOSITIONS FOR TREATING PROGESTERONE-DEPENDENT CONDITIONS

(71) Applicant: REPROS THERAPEUTICS INC., The Woodlands, TX (US)

(72) Inventors: Joseph S. Podolski, The Woodlands, TX (US); Ronald D. Wiehle, Houston, TX (US)

(73) Assignee: REPROS THERAPEUTICS INC., The Woodlands, TX (US)

( * ) Notice: Subject to any disclaimer, the term of this patent is extended or adjusted under 35 U.S.C. 154(b) by 0 days.

(21) Appl. No.: 14/440,023

(22) PCT Filed: Oct. 22, 2013

(86) PCT No.: PCT/US2013/066095
§ 371 (c)(1),
(2) Date: Apr. 30, 2015

(87) PCT Pub. No.: WO2014/070517
PCT Pub. Date: May 8, 2014

(65) Prior Publication Data
US 2015/0297612 A1    Oct. 22, 2015

Related U.S. Application Data

(60) Provisional application No. 61/722,095, filed on Nov. 2, 2012.

(51) Int. Cl.
| | | |
|---|---|---|
| *A61K 31/56* | (2006.01) | |
| *A61K 31/573* | (2006.01) | |
| *A61K 45/06* | (2006.01) | |
| *A61K 31/57* | (2006.01) | |
| *A61K 9/00* | (2006.01) | |
| *A61K 9/14* | (2006.01) | |

(52) U.S. Cl.
CPC .......... *A61K 31/573* (2013.01); *A61K 9/0014* (2013.01); *A61K 9/0034* (2013.01); *A61K 9/0053* (2013.01); *A61K 9/14* (2013.01); *A61K 31/57* (2013.01); *A61K 45/06* (2013.01)

(58) Field of Classification Search
None
See application file for complete search history.

(56) References Cited

U.S. PATENT DOCUMENTS

| | | |
|---|---|---|
| 4,233,296 A | 11/1980 | Teutsch et al. |
| 4,508,703 A | 4/1985 | Redziniak et al. |
| 4,615,697 A | 10/1986 | Robinson |
| 4,621,023 A | 11/1986 | Redziniak et al. |
| 4,954,490 A | 9/1990 | Cook et al. |
| 5,077,211 A | 12/1991 | Yarosh |
| 5,468,741 A | 11/1995 | Yen |
| 6,020,328 A | 2/2000 | Cook et al. |
| 6,043,234 A | 3/2000 | Stockemann et al. |
| 6,451,780 B1 | 9/2002 | Chwalsz et al. |
| 6,455,077 B2 | 9/2002 | Katiyar et al. |
| 6,861,415 B2 | 3/2005 | Kim et al. |
| 6,900,193 B1 | 5/2005 | Kim et al. |
| 8,426,394 B2 * | 4/2013 | Podolski ................ A61K 31/56 514/179 |
| 8,519,004 B2 | 8/2013 | Podolski |
| 8,569,276 B2 | 10/2013 | Kim et al. |
| 2002/0025951 A1 | 2/2002 | Kim et al. |
| 2004/0048841 A1 | 3/2004 | Hoffmann et al. |
| 2005/0143365 A1 | 6/2005 | Kim et al. |
| 2006/0241125 A1 | 10/2006 | Bradley et al. |
| 2007/0103510 A1 | 5/2007 | Silverbrook |
| 2008/0248102 A1 | 10/2008 | Rajewski et al. |
| 2009/0149434 A1 | 6/2009 | Podolski |
| 2011/0046098 A1 | 2/2011 | Podolski |
| 2014/0163114 A1 | 6/2014 | Podolski et al. |

FOREIGN PATENT DOCUMENTS

| | | |
|---|---|---|
| AU | 1997/029304 B2 | 9/1999 |
| AU | 2007/327707 B2 | 7/2012 |
| CN | 1846703 | 10/2006 |
| EP | 0245170 A1 | 11/1987 |
| EP | 1593376 A1 | 11/2005 |
| JP | 9-502724 | 3/1997 |
| JP | 2000-509396 | 7/2000 |
| JP | 2003-529604 | 7/2000 |
| JP | 3143474 | 12/2000 |
| JP | 2008-505718 | 2/2008 |

(Continued)

OTHER PUBLICATIONS

U.S. Appl. No. 12/990,210, filed Oct. 28, 2010 which is a national stage of PCT/US09/041836.
U.S. Appl. No. 12/990,203, filed Oct. 28, 2010, (now U.S. Pat. No. 8,426,394), which is a national stage of PCT/US2009/41826.
U.S. Appl. No. 12/245,089, filed Oct. 3, 2008, (abandoned).
U.S. Appl. No. 13/855,559, filed Apr. 2, 2013, (now U.S. Pat. No. 8,735,381), which is a continuation of U.S. Appl. No. 12/990,203.
U.S. Appl. No. 13/636,119, filed Sep. 19, 2012 which is a national stage of PCT/US2010/062068.
U.S. Appl. No. 13/997,097, filed Jun. 21, 2013 which is a national stage of PCT/US2011/50859.
U.S. Appl. No. 14/664,518, filed Mar. 20, 2015 which is a continuation of U.S. Appl. No. 13/997,087.
U.S. Appl. No. 14/286,535, filed May 23, 2014 which is a continuation of U.S. Appl. No. 12/990,210.
U.S. Appl. No. 14/403,141, filed Nov. 21, 2014 which is a national stage of PCT/US13/043447.
Alexander, et al., "Why consider vaginal drug administration?" Fertility and Sterility, vol. 82, No. 1, pp. 1-12 (2004).

(Continued)

*Primary Examiner* — Heidi Reese
(74) *Attorney, Agent, or Firm* — Morgan, Lewis & Bockius LLP

(57) ABSTRACT

The subject matter of the instant invention is pertinent to the field of treatment of hormone-dependent conditions. Methods for treating these conditions are provided comprising systemically administering an antiprogestin and contemporaneously locally administering an antiprogestin. Embodiments of the instant invention disclose methods for treating endometriosis, dysmenorrhea, breast cancer, uterine fibroids and endometrial hyperproliferation.

18 Claims, 4 Drawing Sheets

(56) References Cited

FOREIGN PATENT DOCUMENTS

| | | | | |
|---|---|---|---|---|
| JP | 2008-509217 | 3/2008 | | |
| JP | 2010-18639 | 1/2010 | | |
| JP | 2010-540430 | 12/2010 | | |
| WO | WO 83/03099 | 9/1983 | | |
| WO | WO 95/07699 | 3/1995 | | |
| WO | WO 97/41145 | 11/1997 | | |
| WO | WO 98/08471 | 3/1998 | | |
| WO | WO 99/45022 | 9/1999 | | |
| WO | WO 00/34036 | 6/2000 | | |
| WO | WO 01/18025 | 3/2001 | | |
| WO | WO 01/24788 | 4/2001 | | |
| WO | WO 01/74840 | 10/2001 | | |
| WO | WO 03/005954 | 1/2003 | | |
| WO | WO 2004/096151 | 11/2004 | | |
| WO | WO 2006/010097 | 1/2006 | | |
| WO | WO 2006/023109 | 3/2006 | | |
| WO | WO 2006/136462 | 12/2006 | | |
| WO | WO 2007/103510 | 9/2007 | | |
| WO | WO 2008/067086 | 6/2008 | | |
| WO | WO 2008/129396 | 10/2008 | | |
| WO | WO 2009/037704 | 3/2009 | | |
| WO | WO 2011/039680 | 4/2011 | | |
| WO | WO 2012/087389 | 6/2012 | | |
| WO | WO 2012087389 A1 * | 6/2012 | ............ | C07J 7/0045 |
| WO | WO 2012/121767 | 9/2012 | | |
| WO | WO 2012121767 A1 * | 9/2012 | ........... | A61K 9/0036 |

OTHER PUBLICATIONS

Attardi, B., et al., "CDB-4124 and Its Putative Monodemthylated Metabolite, CDB-4453, are Potent Antiprogestins with Reduced Antiglucocorticoid Activity: In Vitro Comparison to Mifepristone and CDB-2914", Molecular and Cellular Endocrinology, vol. 188, No. 1-2, pp. 111-123 (Feb. 25, 2002).

Bauerfeind, I., et al., "Endocrine Agents in the Treatment of Advanced Breast Cancer," Gynakologe 199908 DE, vol. 32, No. 8, pp. 605-613 (Aug. 1999).

Benagiano, G., et al., "Selective Progesterone Receptor Modulators 3: Use in Oncology, Endocrinology and Psychiatry," Expert Opinion on Pharmacotherapy, vol. 9, No. 14, pp. 2487-2496 (Oct. 2008).

Bouchard, P., et al., "Selective Progesterone Receptor Modulators in Reproductive Medicine: Pharmacology, Clinical Efficacy and Safety," Fertility and Sterility, vol. 96, No. 5, pp. 1175-1189 (Nov. 2011).

Brueggemeier, R. W., et al., Aromatase Inhibitors in the Treatment of Breast Cancer, Endocrine Reviews, vol. 26, No. 3, pp. 331-345 (May 2005).

Bulun, S., et al., Regulation of Aromatase Expression in Estrogen-Responsive Breast and Uterine Disease: From Bench to Treatment, Pharmacological Reviews, vol. 57, No. 3, pp. 359-383 (Sep. 2005).

Chand, A., et al., "Aromatase Expression is Increased in BRCAI Mutation Carriers," BMC Cancer, vol. 9, p. 1-9 (May 2009).

Donnez, J., et al., "Long-Term Treatment of Uterine Fibroids with Ulipristal Acetate," Fertility and Sterility, vol. 101, No. 6. pp. 1565-1573 (Jun. 2014).

European Search Report for European Application No. 15179121.7 dated Nov. 4, 2015.

Francis, Z., et al., "Contraception of the Future," Reproduction Humaine et Hormones, vol. 21, No. 1 pp. 102-116 (Mar. 2008).

Goodman and Gilman's, The Pharmacological Basis of Therapeutics, 7th Edition, p. 5 and 15 (1985).

Gupta, A., et al., "Efficacy and Mechanism of Action of Proellex, an Antiprogestin in Aromatase Overexpressing and Letrozole Resistant T47 Breast Cancer Cells," Journal of Steroid Biochemistry and Molecular Biology. vol. 133, pp. 30-42 (Jan. 2013).

Heikinheimo, O., Drug Disposition "Clinical Pharmacokinetics of Mifepristone," Clin. Pharmacokinet, No. 1, pp. 7-17 (Jul. 1997).

Heikinheimo, O., et al., "Intravaginal Administration of RU 4868 in Humans and Rats: Inadequate Absorption in Humans, "Hum Reprod., vol. 2, No. 8, pp. 645-7648 (Nov. 1987) Abstract.

Horwitz, K., The Molecular Biology of RU 486. Is There a Role for Antiprogestins in the Treatment of Breast Cancer?, Endocrine Reviews, vol. 13, No. 2, pp. 146-163 (May 1992).

International Preliminary Report on Patentability of PCT/US13/066095 dated May 5, 2015.

International Preliminary Report on Patentability of PCT/US2008/078684 dated May 11, 2010.

International Preliminary Report on Patentability of PCT/US2009/041826 dated Nov. 2, 2010.

International Preliminary Report on Patentability of PCT/US2009/041795 dated Nov. 2, 2010.

International Preliminary Report on Patentability of PCT/US2009/041841 dated Nov. 2, 2010.

International Preliminary Report on Patentability of PCT/US2009/041836 dated Feb. 11, 2010.

International Preliminary Report on Patentability of PCT/US2010/50859 dated Jun. 25, 2013.

International Preliminary Report on Patentability of PCT/US2010/62068 dated Sep. 25, 2012.

International Preliminary Report on Patentability of PCT/US2013/043447 dated Dec. 2, 2014.

International Search Report of PCT/US2008/078684 dated Dec. 22, 2008.

International Search Report of PCT/US2009/041795 dated Jul. 2, 2009.

International Search Report of PCT/US2009/041826 dated Jul. 3, 2009.

International Search Report of PCT/US2009/041836 dated Jul. 3, 2009.

International Search Report of PCT/US2009/041841 dated Oct. 27, 2009.

International Search Report of PCT/US2010/62068 dated Aug. 17, 2011.

International Search Report of PCT/US2011/050859 dated Feb. 27, 2012.

International Search Report of PCT/US2013/043447 dated Aug. 13, 2013.

International Search Report of PCT/US2013/066095 dated Nov. 26, 2013.

Kawaguchi, K., et al., "Mitotic Activity in Uterine Leiomyomas During the Menstrual Cycle," America Journal Obstet. Gynecol., vol. 160, No. 3, pp. 637-641 (Mar. 1989).

Lanari, C., et al., "Antiprogestins in Breast Cancer Treatment: Are We Ready?" Endocrine Related Cancer, vol. 19, No. 3, pp. R35-R50, (Feb. 20, 2012).

Leo, Joyce, C., et al., "The Activities of Progesterone Receptor Isoform A and B are Differentially Modulated by Their Ligands in a Gene-Selective Manner,", International Journal of Cancer, vol. 122, No. 1, pp. 230-243 (Jan. 2008).

Makhsida, N., et al., "Hypogonadism and Metabolic Syndrome: Implications for Testosterone Therapy," the Journal of Urology, vol. 174, Issue 3, pp. 827-834 (Sep. 2005).

Mizutani, T., M.D., et al., "Danazol Concentrations in Ovary, Uterus, and Serum and Their Effect on the Hypothalamic-Pituitary-Ovarian Axis During Vaginal Adminsitraiton of a Danazol Suppository," Fertility and Sterility, vol. 63, No. 6, pp. 1184-1189 (Jun. 1995).

Mealy, N., et al., "CDB-4124," Drugs of the Future, vol. 29, No. 11, pp. 1133 (Nov. 2004).

Nabholtz, J. M., et al., "Anastrozole (Arimidex™) versus Tamoxifen as First-Line Therapy for Advanced Breast Cancer in Postmenopausal Women: Survival Analysis and Updated Safety Results," European Journal of Cancer, vol. 39, No. 12, pp. 1684-1689 (Aug. 2003).

Nelson, A., "Extended-Cycle Oral Contraception—A New Option for Routine Use," Treatments in Endocrinology, vol. 4, No. 3, pp. 139-145 (Jun. 2005).

Passaro, M., et al., "Luteal Phase Dose-Response Relationships of the Antiprogestin CDB-2914 in Normally Cycling Women," Human Reproduction, vol. 18, No. 9, pp. 1820-1827 (Sep. 2003).

Rose, C., et al., "An Open Randomised Trial of Second-Line Endocrine Therapy in Advanced Breast Cancer—Comparison of the

(56) References Cited

OTHER PUBLICATIONS

Aromatase Inhibitors Letrozole and Anastrozole" European Journal of Cancer, vol. 39, No. 16, pp. 2318-2327 (Nov. 2003).
Santos, A., et al., "Anastrozole as Neoadjuvant Therapy for Patients with Hormone-Dependent, Locally-Advanced Breast Cancer," Anticancer Research, vol. 24, pp. 1315-1318 (Mar. 2004).
Spitz, Irving M.,"Clinical Utility of Progesterone Receptor Moulators and Their Effect on the Endometrium," Current Opinion in Obstetrics & Gynecology, vol. 21, No. 4, pp. 318-324 (Aug. 2009).
Spitz., Irving M., "Progesterone Receptor Antagonists," Current Opinion in Investigational Drugs, vol. 7, No. 10, pp. 882-890 (Oct. 2006).
Wiehle, R., et al., "CDB-4124, A Progesterone Receptor Modulator, Inhibits Mammary Carcinogenesis by Suppressing Cell Proliferation and Inducing Apoptosis," Cancer Prevention Research, vol. 4, No. 3, pp. 414-424 (Mar. 2011).
Wiehle, Ronald, et al., "Anti-Progestins Suppress the Growth of Established Tumors Induced by 7,12-dimethylbenz(a)anthracene: comparison between RU486 and a new 21-substituted-19-norprogestin," Oncology Reports, vol. 18, No. 1, pp. 167-174 (Jul. 2007).
Written Opinion of PCT/US09/041826 dated Oct. 28, 2010.
Written Opinion of PCT/US09/041795 dated Oct. 28, 2010.
Written Opinion of PCT/US09/041841 dated Oct. 28, 2010.
Written Opinion of PCT/US11/050859 dated Jun. 23, 2013.
Written Opinion of PCT/US2008/078684 dated May 5, 2010.
Written Opinion of PCT/US2013/066095 dated Nov. 26, 2013.
Written Opinion of PCT/US2009/041836 dated Jul. 3, 2009.
Written Opinion of PCT/US2010/62068 dated Aug. 17, 2011.
Written Opinion of PCT/US2013/043447 dated Aug. 13, 2013.
Repros Therapeutics Inc. Announces That Proellex Administered to Patients as Cyclic Therapy to Treat the Symptoms of Uterine Fibroids for Up to 30 Months Shows No Adverse Effects on the Endometrium, Drug Information Online—Drugs.com, pp. 1-2 (Jul. 2008).

U.S. Appl. No. 12/990,203—Non-Final office action dated Jun. 1, 2012.
U.S. Appl. No. 12/990,203—Notice of Allowance dated Dec. 26, 2012.
U.S. Appl. No. 12/990,210—Final Office Action dated Feb. 26, 2015.
U.S. Appl. No. 12/990,210—Non-final office action dated Aug. 7, 2013.
U.S. Appl. No. 12/990,210—Non-final office action dated Dec. 4, 2012.
U.S. Appl. No. 12/990,210—Restriction Requirement dated Apr. 24, 2012.
U.S. Appl. No. 12/245,089—Restriction Requirement dated Jun. 4, 2010.
U.S. Appl. No. 12/245,089—Non-Final Office Action dated Sep. 7, 2010.
U.S. Appl. No. 13/636,119—Restriction Requirement dated Dec. 11, 2014.
U.S. Appl. No. 13/636,119—Non-final office action dated Apr. 7, 2015.
U.S. Appl. No. 13/636,119—Final Office Action dated Jul. 9, 2015.
U.S. Appl. No. 13/636,119—Non-final Office Action dated Dec. 11, 2015.
U.S. Appl. No. 13/855,559—Notice of Allowance dated Feb. 23, 2013.
U.S. Appl. No. 13/997,097—Non-final office action dated Sep. 22, 2014.
U.S. Appl. No. 14/664,518—Non-final office action dated May 18, 2016.
U.S. Appl. No. 14/286,535—Non-final office action dated Nov. 6, 2015.
U.S. Appl. No. 14/440,023—Non-final office action dated Feb. 16, 2016.
U.S. Appl. No. 14/403,141—Restriction Requirement dated Mar. 22, 2016.

\* cited by examiner

METHODS AND COMPOSITIONS FOR TREATING PROGESTERONE-DEPENDENT CONDITIONS

CROSS-REFERENCE TO RELATED APPLICATIONS

This application claims the benefit of U.S. Provisional Application No. 61/722,095, filed Nov. 2, 2012, the contents of which are incorporated herein by reference.

FIELD OF THE INVENTION

In several embodiments, the present invention relates to improved antiprogestin administration regimens for treating progesterone-dependent conditions comprising contemporaneous local and systemic administration of the antiprogestin.

BACKGROUND OF THE INVENTION

The effect of the steroid hormone progesterone on the reproductive system has been well-documented. For example, progesterone is vital to establishing and maintaining pregnancy and exerts actions on various tissues of the reproductive system. The action of progesterone on tissues outside the reproductive system has been reported but is less well characterized.

Antiprogestins, compounds which inhibit the action of progesterone, have considerable potential for use in the pharmacological regulation of fertility and a variety of conditions and diseases such as breast cancer and endometriosis. The first reported antiprogestin, mifepristone (RU 486), is one of a number of 19-nortestsosterone derivatives with strong affinity for both the progesterone and glucocorticoid receptors and with antiprogestational and antiglucocorticoid activity. A variety of antiprogestins based on the 19-norprogesterone backbone have also been synthesized.

Several drawbacks are associated with current antiprogestin administration regimes. If these and other limitations associated with antiprogestin treatment could be improved, a significant advance in the treatment of hormone-dependent disorders would result.

SUMMARY OF THE INVENTION

In several embodiments, the present invention provides methods for preventing or treating a hormone (i.e. estrogen and/or progesterone) dependent condition comprising systemically administering an antiprogestin to a patient in need of such treatment and contemporaneously administering an antiprogestin locally to the patient. In related embodiments, systemic administration occurs daily or every other day and local administration of the antiprogestin occurs by daily, periodic or intermittent dosing scheme. A preferred antiprogestin for use in the methods is CDB-4124 (21-methoxy-17α-acetoxy-11β-(4 N, N-dimethylaminophenyl)-19-norpregna-4,9-diene-3,20-dione; telapristone). A preferred salt of CDB-4124 for use in the methods is the acetate salt (telapristone acetate).

In some embodiments, the antiprogestin is administered systemically by oral administration. In preferred embodiments, the present invention provides methods for treating or preventing a hormone dependent disorder comprising orally administering an antiprogestin and contemporaneously administering an antiprogestin locally to the patient wherein: the antiprogestin is orally administered for a period beginning during the luteal phase of the subject's menstrual cycle and ending at least one week after the menstrual phase of the subsequent cycle and the antiprogestin is locally administered for a period beginning less than one week after the menstrual phase of the subsequent cycle and continuing until the end of the treatment period. Oral administration of the antiprogestin preferably occurs by daily administration of a dose of from about 1 mg to about 25 mg, preferably from about 3 mg to about 12.5 mg.

In other embodiments, the antiprogestin is administered locally by administration to the vaginal mucosa or breast tissue. In preferred embodiments, the present invention provides methods for treating or preventing a hormone dependent disorder comprising orally administering an antiprogestin and contemporaneously administering an antiprogestin to the vaginal mucosa or breast tissue of the patient. Local administration preferably occurs by daily administration of a dose of from about 1 mg to about 25 mg, preferably from about 3 to about 20 mg, more preferably from about 3 mg to about 15 mg, more preferably at about 3, 6, or 12 mg. In some embodiments, the locally administered antiprogestin is in the form of a suppository, a gel, a cream, a transdermal patch or a bioadhesive carrier.

In a particularly preferred embodiment, the present invention provides a method for treating or preventing a hormone dependent disorder comprising orally administering an antiprogestin and contemporaneously administering an antiprogestin vaginally to the patient wherein: the antiprogestin is orally administered for a period beginning during the luteal phase of the subject's menstrual cycle and ending about 1-3 weeks after the menstrual phase of the subsequent cycle at a dose of from about 3 mg to about 25 mg per day and the antiprogestin is vaginally administered for a period beginning less than one week after the menstrual phase of the subsequent cycle and continuing until the end of the treatment period at a dosage of from about 3 mg to about 25 mg per day.

In several embodiments, the treatment period is 1, 2, 3, 4, 5, 6, 7, 8, 9, 10, 11, or 12 months, 2, 3, 4, or 5 years or any range there between.

Hormone-dependent conditions that may be treated by compositions of the invention include, without limitation, endometriosis and pain associated therewith, adenomyosis, endometriomas of the ovary, dysmenorrhea, endocrine hormone-dependent tumors, uterine fibroids, endometrial hyperproliferation, ovarian cancer, cervical cancer and breast cancer. Compositions of the instant invention may also be used to induce menses, to induce labor and for contraception.

BRIEF DESCRIPTION OF THE DRAWINGS

FIG. 2 also illustrates the actual Cmax observed for Proellex (CDB-4124) and its monodemethylated metabolite CDB-4453, following vaginal administration of CDB-4124 at 12.5 mg, 25 mg and 50 mg doses.

DETAILED DESCRIPTION OF THE INVENTION

Figure 1:
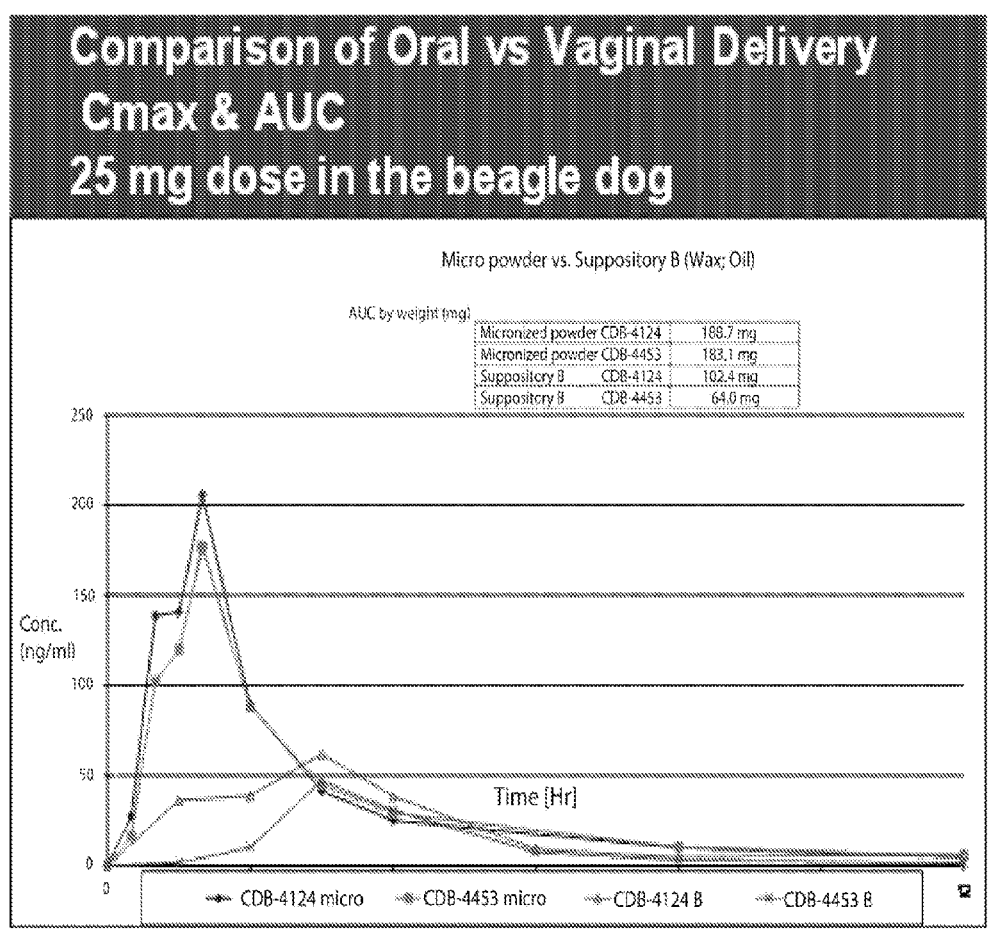
FIG. 1 illustrates a comparison of the Cmax (peak serum concentration) and area under the curve (AUC) following oral and vaginal administration of CDB-4124 or CDB-4453 at a 25 mg dose in beagles.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges and ranges of ratios can be unambiguously derived form the data and numbers presented herein and all represent embodiments of the invention.

Before the present compounds, compositions and methods are disclosed and described, it is to be understood that the terminology used herein is for the purpose of describing particular embodiments only and is not intended to be limiting. It must be noted that, as used in the present specification and the appended claims, the singular forms "a," "an" and "the" include plural referents unless the context clearly dictates otherwise.

DEFINITIONS

The term "oral" administration means that the active agent is in a formulation designed to be ingested, i.e. designed to be delivered to the gastrointestinal system for absorption.

The term "effective dosage" means an amount of the composition's active component sufficient to treat a particular condition.

The term "selective progesterone receptor modulators" means compounds that affect functions of progesterone receptor in a tissue-specific manner. The compounds act as progesterone receptor antagonists in some tissues (for example, in breast tissue) and as progesterone receptor agonists in other tissues (for example, in the uterus).

The term "treat" or "treatment" as used herein refers to any treatment of any hormone-dependent disorder or disease, and includes, but is not limited to, inhibiting the disorder or disease arresting the development of the disorder or disease; relieving the disorder or disease, for example, causing regression of the disorder or disease; or relieving the condition caused by the disease or disorder, relieving the symptoms of the disease or disorder.

The term "prevent" or "prevention," in relation to a hormone-dependent disorder or disease, means preventing the onset of disorder or disease development if none had occurred, or preventing further disorder or disease development if the disorder or disease was already present. For example, compositions of the present invention may be used to prevent the recurrence of tumors. Recurrence of tumors may occur because of residual microscopic groups or nests of tumor cells which subsequently expand into clinically detectable tumors.

The present invention provides methods for treating or preventing hormone-dependent conditions including without limitation, endometriosis and pain associated therewith, dysfunctional uterine bleeding, adenomyosis, endometriomas of the ovary, dysmenorrhea, endocrine hormone-dependent tumors, uterine fibroids, endometrial hyperproliferation, ovarian cancer, cervical cancer and breast cancer. The methods are particularly useful for treating endometriosis (and pain associated therewith), dysfunctional uterine bleeding and uterine fibroids.

In several embodiments, the present methods utilize one or more progesterone antagonists, defined herein as compounds that bind to a progesterone receptor and inhibit the effect of progesterone. Progesterone antagonists include so-called "pure" antiprogestins such as mifepristone, as well as selective progesterone receptor modulators (SPRMs) such as asoprisnil and CDB-4124 which may act as progesterone receptor agonists in certain tissues and progesterone receptor antagonists in others. The methods are particularly useful for long-term (chronic) administration of selective progesterone receptors.

Non-limiting examples of progesterone antagonists include the steroid compounds disclosed in U.S. Pat. Nos. 6,861,415 and 6,900,193, the contents of which are incorporated herein by reference. In a preferred embodiment, the steroid compound is CDB-4124 (21-methoxy-17α-acetoxy-11β-(4 N, N-dimethylaminophenyl)-19-norpregna-4,9-diene-3,20-dione; telapristone) or CDB-4453 (21-methoxy-17α-acetoxy-11β-(4-N-methylaminophenyl)-19-norpregna-4,9-diene-3,20-dione).

Other preferred progesterone antagonists for practicing the methods of the invention include, without limitation, Mifepristone (RU-486; 11β-[4 N,N-dimethylaminophenyl]-17β-hydroxy-17-(1-propynyl)-estra-4,9-dien-3-one), Lilopristone (11β-(4 N,N-dimethylaminophenyl)-17β-hydroxy-17-((Z)-3-hydroxypropenyl)estra-4,9-dien-3-one), Onapristone (11β-(4 N,N-dimethylaminophenyl)-17α-hydroxy-17-(3-hydroxypropyl)-13α-estra-4,9-dien-3-one), asoprisnil (benzaldehyde, 4-[(11β,17β)-17-methoxy-17-(methoxymethyl)-3-oxoestra-4,9-dien-11-yl]-1-(E)-oxim; J867), its metabolite J912 (4-[17β-Hydroxy-17α-(methoxymethyl)-3-oxoestra-4,9-dien-11β-yl]benzaldehyd-(1E)-oxim) and CDB-2914 (17α-acetoxy-11β-(4-N,N-dimethylaminophenyl)-19-norpregna-4,9-dien-3,20-dione).

Other antiprogestins include compounds described in U.S. Pat. Nos. 4,386,085, 4,447,424, 4,536,401, 4,519,946, 4,609,651, 4,634,695, 4,780,461, 4,814,327, 4,829,060, 4,871,724, 4,921,845, 4,921,845, 5,095,129, 5,446,178, 5,478,956, 5,232,915 5,089,488, 5,093,507, 5,244,886, 5,292,878, 5,439,913, 5,446,036, 5,576,310; 5,684,151, 5,688,808, 5,693,646, 5,693,647, 5,696,127, 5,696,130, 5,696,133 5,739,125, 5,407,928, 5,273,971, 5,728,689, 5,753,655, 5,843,933, 5,843,931, 6,509,334, 6,566,358, 6,713,478, 6,391,907, 6,417,214, 6,380,235, 6,339,098, 6,306,851, 6,441,019, 6,369,056, and 6,358,948, the contents of each of which are incorporated herein by reference.

Yet other antiprogestins useful in practicing the methods of the invention, include without limitation JNJ-1250132, (6α,11β,17β)-11-(4-dimethylaminophenyl)-6-methyl-4',5'-dihydrospiro[estra-4,9-diene-17,2'(3'H)-furan]-3-one (ORG-31710); (11β,17α)-11-(4-acetylphenyl)-17,23-epoxy-19,24-dinorchola-4,9,20-trien-3-one (ORG-33628); (7β,11β,17β)-11-(4-dimethylaminophenyl-7-methyl]-4',5'-dihydrospiro[estra-4,9-diene-17,2'(3'H)-furan]-3-one (ORG-31806); ZK-112993; ORG-31376; ORG-33245; ORG-31167; ORG-31343; RU-2992; RU-1479; RU-25056; RU-49295; RU-46556; RU-26819; LG1127; LG120753; LG120830; LG1447; LG121046; CGP-19984A; RTI-3021-012; RTI-3021-022; RTI-3021-020; RWJ-25333; ZK-136796; ZK-114043; ZK-230211; ZK-136798; ZK-98229; ZK-98734; ZK-137316; 4-[17β-Methoxy-17α-(methoxymethyl)-3-oxoestra-4,9-dien-11β-yl]benzaldehyde-1-(E)-oxime; 4-[17β-Methoxy-17α-(methoxymethyl)-3-oxoestra-4,9-dien-11β-yl]benzaldehyde-1-(E)-[O-(ethylamino)carbonyl]oxime; 4-[17β-Methoxy-17α-(methoxymethyl)-3-oxoestra-4,9-dien-11β-yl]benzaldehyde-1-(E)-[O-(ethylthio)carbonyl]oxime; (Z)-6'-(4-cyanophenyl)-9,11α-dihydro-17β-hydroxy-17α-[4-(1-oxo-3-methylbutoxy)-1-butenyl]4'H-naphtho[3',2',1'; 10,9,11]estr-4-en-3-one; 11β-(4-acetylphenyl)-17β-hydroxy-17α-(1,1,2,2,2-pentafluoroethyl)estra-4,9-dien-3-one; 11beta-(4-Acetylphenyl)-19,24-dinor-17,23-epoxy-17alpha-chola-4,9,20-trien-3-one; (Z)-11beta,19-[4-(3-Pyridinyl)-o-phenylene]-17beta-hydroxy-17α-[3-hydroxy-1-propenyl]-4-androsten-3-one; 11beta-[4-(1-methylethenyl)phenyl]-17α-hydroxy-17beta-β-hydroxypropyl)-13α-estra-4,9-dien-3-one; 4',5'-Dihydro-11beta-[4-(dimethylamino)phenyl]-6beta-methylspiro[estra-4,9-dien-17beta,2'(3'H)-furan]-3-one.

In some embodiments a single progesterone antagonist is administered systemically and the identical progesterone antagonist is locally administered. In a preferred embodiment, CDB-4124 is administered systemically, preferably by the oral route, and CDB-4124 is contemporaneously administered locally, preferably vaginally or transdermally to the breast. In other embodiments, a single progesterone antagonist is administered systemically and a different progesterone antagonist is locally administered.

Also useful with the methods of the invention are salts of progesterone antagonists. Depending on the process conditions the salt compound obtained may be either in neutral or salt form. Salt forms include hydrates and other solvates and also crystalline polymorphs. Both the free base and the salts of these end products may be used in accordance with the invention.

Acid addition salts may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbensensulfonic acid, toluenesulfonic acid, galactaric acid, galacturonic acid or naphthalenesulfonic acid. All crystalline form polymorphs may be used in accordance with the invention. A preferred salt is the acetate salt.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines. Examples of metals used as cations are sodium, potassium, calcium, magnesium and the like. Examples of suitable amines are amino acids such as lysine, choline, diethanolamine, ethylenediamine, N-methylglucamine and the like.

Systemic and local administration of the progesterone antagonist may be independently accomplished by daily administration, periodic administration (i.e., administration at uniform intervals less frequent than daily such as every other day, weekly, bi-weekly or monthly) or intermittent administration by which it is meant that the progesterone antagonist is administered daily or periodically for an administration period then administration of the progesterone antagonist is discontinued for a period of time greater than the dosing interval during the previous administration period but less than the administration period, then the progesterone antagonist is administered daily or periodically for an administration period, then administration is discontinued and so on. For the treatment of endometriosis and pain associated therewith, adenomyosis, endometriomas of the ovary, dysmenorrhea, uterine fibroids, endometrial hyperproliferation, ovarian cancer, and cervical cancer, systemic administration is preferably accomplished by administering the progesterone antagonist daily or every other day, preferably orally.

For the treatment of endometriosis and pain associated therewith, adenomyosis, endometriomas of the ovary, dysmenorrhea, uterine fibroids, endometrial hyperproliferation, ovarian cancer, and cervical cancer, a progesterone antagonist is administered orally for a period beginning during the luteal phase of the female's menstrual cycle and ending during the follicular, ovulatory or luteal phase of the subsequent cycle, preferably between 1 to 3 weeks after the menstrual phase of the subsequent cycle. In other embodiments, the progesterone antagonist is administered orally for a period beginning during the luteal phase of the female's menstrual cycle and continuing for about 3-5 weeks, preferably about 4 weeks, after which oral administration is discontinued. In related embodiments, a progesterone antagonist is contemporaneously administered vaginally for a period beginning during the menstrual phase or follicular phase of the subsequent cycle, preferably within one week after the menstrual phase of the subsequent cycle and ending when the desired therapeutic effect is achieved. In certain embodiments, the progesterone antagonist is administered vaginally for an administration period of at least 1, 2, 3, 4, 5, 6, 7, 8, 9, 10, 11, 12 or more months and even for a period of at least 1, 2, 3, 4, 5, 6, 7, 8, 9, 10 or more years. In related embodiments, oral and vaginal administration each occurs by daily administration of a progesterone antagonist at dose of from 3 to 25 mg.

In a particularly preferred embodiment, CDB-4124 is administered daily at a dose of 3 mg to 25 mg to a female patient by the oral route for a period beginning on day 16 to 28 of a female's menstrual cycle and ending on day 11-25 of the subsequent cycle and CDB-4124 is contemporaneously administered vaginally beginning on day 1-10, preferably day 2-10, more preferably day 3-7 of the subsequent cycle and continuing until a desired therapeutic effect is achieved in order to treat endometriosis and pain associated therewith, adenomyosis, endometriomas of the ovary, dysmenorrhea, uterine fibroids, endometrial hyperproliferation, ovarian cancer, or cervical cancer. Preferably, no further oral administration of CDB-4124 occurs after day 11-25 of the subsequent cycle.

In another preferred embodiment, a method for treating breast cancer is provided comprising oral and contemporaneous transdermal administration of CDB-4124 to a breast tumor wherein oral and transdermal administration independently occur by daily administration, periodic administration or intermittent administration. In some embodiments, oral and transdermal administration occur by daily administration.

The contemporaneous systemic and local administration of antiprogestins provides several important advantages. Systemic administration of antiprogestins, particularly by the oral route, subjects the drug to metabolism by gastrointestinal and hepatic enzymes which results in a significant reduction in the effective concentration of unmetabolized drug. This "first pass" effect results in a need to administer a correspondingly higher dose of the drug to achieve therapeutic effect—these higher doses can result in liver damage when the antiprogestin is administered chronically. Local administration, particularly vaginal administration, avoids first pass effects and consequently a lower dose can be administered directly to the site where the drug's effect is desired. However, the present inventors have discovered that, when progesterone antagonists are administered locally, e.g. vaginally, the onset of therapeutic benefit is delayed, apparently because an effective concentration of the drug is not immediately achieved. The methods of the present invention provide a solution to this problem by combining a relatively brief period of systemic (e.g. oral) administration of the progesterone antagonist (e.g. orally) beginning during the luteal phase of the female's menstrual cycle and contemporaneously initiating long term local (e.g.; vaginal) administration of the progesterone antagonist. Thus, following an initial menses at the beginning of the subsequent menstrual cycle which acts to refresh the endometrium and prevent subsequent adverse endometrial events, the therapeutic effect of the antiprogestin is expedited relative to when the antiprogestin is only administered locally.

Contemporaneous systemic and local administration of antiprogestins to treat hormonally responsive breast cancer (i.e. the breast tumor contains estrogen and/or progesterone receptor) has advantages as well. The present inventors have discovered that oral administration of a relatively low dose (about 3-25 mg) of an SPRM, CDB-4124, is able to partially but not completely suppress ovulation through central effects on the hypothalamic pituitary axis (HPA) without the toxic liver effects that accompany chronic oral administration at higher doses; ovarian estrogens are lowered but not suppressed to the low levels typical of menopausal women. The present inventors have also discovered that CDB-4124 is surprisingly active when delivered locally (non-orally) despite achieving systemic levels only a very small fraction of an equivalent oral dose. Contemporaneous local and systemic administration therefore provides a surprisingly effective means of treating breast cancer that avoids toxic liver side effects and side effects that occur when serum estrogen levels are drastically reduced.

In some embodiments, local administration of the progesterone is intermittent such that the subject undergoes menses during at least two discontinuance periods. At least two, and preferably every discontinuance period is of sufficient length for the subject to experience menstruation. More preferably, the subject experiences menstruation during every discontinuance period. In a particularly preferred embodiment, local administration of the progesterone antagonist comprises daily administration to the vagina for an administration period of four months, followed by a discontinuance period during which the subject experiences menstruation, followed by another administration period of four months and so on.

Therapeutically effective doses of the antiprogestin when administered locally may be less than 50 mg/day, less than 40 mg/day, less than 30 mg/day less than 20 mg/day, less than 10 mg/day, less than 5 mg/day, between 5 mg/day and 50 mg/day, between 5 mg/day and 40 mg/day, between 5 mg/day and 30 mg/day, between 5 mg/day and 20 mg/day, or between 5 mg/day and 10 mg/day. In another related embodiment, the effective amount of the compound when administered locally is less than the effective amount when administered systemically, for example, the effective amount when administered locally to the vaginal mucosa may be 2-fold, 3-fold, 4-fold 5-fold, 6-fold, 7-fold, 8-fold, 9-fold and even 10-fold less than the effective amount when administered systemically to treat endometriosis, uterine fibroids and other diseases located in that region.

In one embodiment of the invention, a progesterone receptor antagonist is administered to a female patient in need thereof according to the present methods in order to suppress endometrial proliferation. In a preferred embodiment, the progesterone receptor antagonist is a selective progesterone receptor modulator (SPRM), more preferably CDB-4124, at a systemic and local dose of from about 5 to about 25 mg.

In a related embodiment of the invention, a progesterone receptor antagonist is administered to a female patient in need thereof according to the present methods in order to treat endometriosis. In a preferred embodiment, the progesterone receptor antagonist is an SPRM, more preferably CDB-4124 at a systemic and local dose of from about 3 to about 25 mg.

In a related embodiment of the invention, a progesterone receptor antagonist is administered to a female patient in need thereof according to the present methods in order to treat dysmenorrhea. In a preferred embodiment, the progesterone receptor antagonist is an SPRM, more preferably CDB-4124 at a systemic and local dose of from about 3 to about 25 mg.

In yet another embodiment of the invention, a progesterone receptor antagonist is administered to a female patient in need thereof according to the present methods in order to treat uterine fibroids. In a preferred embodiment, the progesterone receptor antagonist is an SPRM, more preferably CDB-4124 at a systemic and local dose of from about 3 to about 25 mg.

In yet another embodiment of the invention, a progesterone receptor antagonist is administered to a female patient in need thereof according to the present methods in order to treat dysfunctional uterine bleeding. In a preferred embodiment, the progesterone receptor antagonist is an SPRM, more preferably CDB-4124 at a systemic and local dose of from about 3 to about 25 mg For local administration, the progesterone antagonist may be prepared in any formulation suitable for local administration. For example, the compound may be formulated, without limitation, as an intravaginal preparation such as a doughnut-shaped hormone-releasing vaginal ring; a vaginal suppository; a vaginal pill; an intrauterine preparation such as an intrauterine device (IUD) or matrix preparation; an implantable drug delivery device; a topical gel; a cream, an ointment, a trans-dermal patch or in a bioadhesive carrier such as those described in U.S. Pat. No. 4,615,697, which is incorporated herein by reference. The bioadhesive carrier may be in gel, cream, tablet, pill, capsule (e.g. pullulan capsule), suppository, or film form or any other pharmaceutically acceptable form that will adhere to the vaginal mucosa. Preferably the formulation comprises a unit dose of the progesterone antagonist of between 3 mg and 25 mg, or any range there between, such as 3 mg, 5 mg, 8 mg, 12 mg, 15 mg, 20 mg or 25 mg and one or more pharmaceutically acceptable carriers.

For systemic administration, the progesterone antagonist may be prepared in the form of a dose unit or dose units suitable for systemic administration. For example, the compound may be formulated in a solid dosage unit suitable for oral administration such as a tablet (e.g. standard hard tablets, suspension tablets, rapid dispersion tablets, chewable tablets, effervescent tablets, bilayer tablets, etc.), caplet, capsule (e.g., a soft or a hard gelatin capsule), powder (e.g. a packaged powder, a dispensable powder or an effervescent powder), lozenge, sachet, cachet, troche, pellet granules, microgranules, encapsulated microgranules, or any other solid dosage form. Alternatively, the compound may be formulated in suitable liquid dosage forms such as solutions, aqueous suspensions, elixirs, syrups, etc. Preferably the formulation comprises a unit dose of the progesterone antagonist of between 3 mg and 25 mg, or any range there between, such as 3 mg, 5 mg, 8 mg, 12 mg, 15 mg, 20 mg or 25 mg and one or more pharmaceutically acceptable carriers. The systemic administration dose should in any event be lower than the effective dose when administered systemically in the absence of contemporaneous local administration.

Compositions of the invention can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition. Excipients include, by way of illustration and not limitation, diluents, disintegrants, binding agents, adhesives (e.g. bioadhesives), wetting agents, lubricants, glidants, surface modifying agents or surfactants, fragrances, suspending agents, emulsifying agents, nonaqueous vehicles, preservatives, antioxidants, adhesives, agents to adjust pH and osmolarity (e.g. buffering agents), preservatives, thickening agents, sweetening agents, flavoring agents, taste masking agents, colorants or dyes, penetration enhancers and substances added to improve appearance of the composition.

A therapeutically effective amount of the composition required for use in therapy varies with the length of time that activity is desired, and the age and the condition of the patient to be treated, among other factors, and is ultimately determined by the attendant physician. In general, however, doses employed for human treatment typically are in the range of about 0.001 mg/kg to about 500 mg/kg per day, for example about 1 µg/kg to about 1 mg/kg per day or about 1 µg/kg to about 100 µg/kg per day. For most large mammals, the total daily dosage is from about 1 to 100 mg, preferably from about 2 to 80 mg, more preferably from about 3 to about 25 mg. The dosage regimen may be adjusted to provide the optimal therapeutic response. The desired dose may be conveniently administered in a single dose, or as multiple doses administered at appropriate intervals, for example as two, three, four or more subdoses per day.

Patients undergoing treatments with the compositions of the instant invention should be monitored routinely for their serum estrogen and glucocorticoid levels.

The following non-limiting examples are provided to aid in understanding the teachings of the instant invention.

Example 1

Measuring In Vitro Binding Affinities of Antiprogestins

Competitive binding assays are performed using cytosolic preparations.

For measuring binding to rabbit progesterone receptor (PR) and glucocorticoid receptor (GR), cytosol is prepared from uterus or thymus, respectively, of estradiol-primed immature rabbits. For binding to rabbit uterine PR, cytosol containing rabbit uterine PR is prepared in TEGMD buffer (10 mM Tris, pH 7.2, 1.5 mM EDTA, 0.2 mM sodium molybdate, 10% glycerol, 1 mM DTT) and incubated with 6 nM 1,2-[$^3$H]progesterone (NEN Life Science Products; 52 Ci/mmol); test compounds are added at concentrations from 2 to 100 nM. For binding to rabbit thymic GR, cytosol is prepared in TEGMD buffer and incubated with 6 nM 6,7-[$^3$H]dex (NEN; 35 or 40 Ci/mmol); test compounds are added at concentrations from 2 to 100 nM.

For measuring binding to human progesterone receptor-A (rhPR-A) or progesterone receptor-B (rhPR-B), cytosolic extracts from Sf9 insect cells infected with recombinant baculovirus expressing either hPR-A or hPR-B is prepared. Sf9 cytosol (prepared in TEGMD buffer containing the following protease inhibitors: bacitracin at 100 µg/ml, aprotinin at 2 µg/ml, leupeptin at 94 µg/ml, pepstatin A at 200 µg/ml) is incubated with 6.8 nM 1,2,6,7,16,17-[$^3$H]progesterone (NEN; 143 Ci/mmol); test compounds are added at concentrations from 1 to 100 nM.

After overnight incubation at 4 C, bound and unbound [$^3$H]-steroids are separated by addition of dextran-coated charcoal and centrifugation at 2100×g for 15 minutes at 4 C. Supernatants from GR assays are decanted and counted in a Beckman LS-1800 liquid scintillation counter. Supernatants containing PR are pipetted into 24-well microplates and counted in a Packard TopCount liquid scintillation counter. Counts per minute (cpm) are entered into Packard's RIASmart™ for calculation of $EC_{50}$'s. Relative binding affinity for each test compound is calculated as follows: ($EC_{50}$ of standard)/($EC_{50}$ of competitor)×100. The standard for the PR binding assays is P4 and the standard for the GR binding assays is dex.

Example 2

Measuring Antiglucocorticoid Activity and Progesterone Antagonist Activity In Vivo For measuring in vivo progesterone antagonist activity of test compounds, T47D-CO human breast cancer cells, grown in monolayer culture in phenol red-free DMEM supplemented with 10% fetal bovine serum (FBS), 10 U/ml penicillin G and 10 µg/ml streptomycin sulfate, are transfected with a suitable hormone sensitive reporter gene plasmid, for example $PRE_2$-tk-LUC, which contains two copies of a progestin/glucocorticoid/androgen response element upstream of the thymidine kinase (tk) promoter and the firefly luciferase (LUC) reporter gene. Transfected T47D-CO cells are incubated with a (predetermined) maximum stimulatory concentration of a progestogen, for example $P_4$, in the absence or presence of various concentrations of test compound for 20 hours. LUC activity is determined using Promega's Luciferase Assay System and the $IC_{50}$ of the test compound is determined.

For measuring in vivo glucocorticoid antagonist activity, HepG2 human hepatoblastoma cells, grown in monolayer culture in phenol red-free MEMα supplemented with 10% FBS and pen/strep, are cotransfected with a suitable hormone sensitive reporter gene plasmid such as $PRE_2$-tk-LUC and a GR expression plasmid. Transfected HepG2 cells are incubated with a (predetermined) maximum stimulatory concentration of dexamethasone in the absence or presence of various concentrations of test compound for 20 hours. $IC_{50}$ of the test compound is determined by measuring LUC activity.

Example 3

Chronic Daily Administration of CDB-4124 is Associated with Toxic Liver Effects

Initial studies conducted with Proellex (aka CDB-4124) demonstrated efficacy of the drug at every dose tested. Development of Proellex has focused on the two highest doses tested, 25 mg and 50 mg based on data suggesting that higher doses suppressed endometrial thickening and the potential for breakthrough uterine bleeding. Neither animal preclinical studies nor small trials in women in Europe at the higher doses for periods of up to six months of exposure predicted the liver toxicity exhibited in the Phase III clinical studies conducted in a diverse population in the United States. Proellex, delivered orally at a dose of 50 mg/day, exhibited severe liver toxicity in roughly 3-4% of the women receiving this dose. At 12.5 mg there were no adverse liver toxicity signals different from placebo. The maximum concentrations of CDB-4124 and its mono-demethylated metabolite (CDB-4453) for the 12.5 mg dose were 25% of the 50 mg dose. All liver toxicities resolved in those women that returned for safety follow-ups, including those subjects that developed liver-associated serious adverse effects (SAEs). The effects observed when Proellex was administered orally at 50 mg/day were significantly lower in frequency and intensity when Proellex was delivered at 25 mg/day. This observation was further amplified by the fact that longer durations of exposure have been safely achieved at a 25 mg/day dose than at a 50 mg/day dose suggesting that duration of exposure at lower doses does not necessarily result in the same liver toxicity than that observed at the 50 mg/day dose.

To date, over 600 patients, including women with confirmed cases of endometriosis or uterine fibroids, have participated in double blind and open label clinical trials in which patients were administered daily oral capsules containing doses of 12.5 mg, 25 mg or 50 mg CDB-4124 (Proellex) for over one month. Of these patients, about 500 received Proellex and about 130 received a placebo. Of the patients receiving Proellex, about 190 received a dose of 50 mg CDB-4124 per day, about 260 received a dose of 25 mg CDB-4124 per day and about 55 received a dose of 12.5 mg per day.

Liver enzymes were frequently monitored in participating subjects. The liver enzyme level at which the clinical trials would be discontinued was set at an increase in liver aminotransferases greater than, or equal to three times the Upper Limit of Normal (≥3×ULN).

During clinical trials, thirteen subjects were found to exhibit an increase in liver enzymes ≥3×ULN, but this was confirmed by a repeat test in 48 hours in only nine subjects. Of the nine subjects with a confirmed increase in liver enzymes ≥3×ULN, seven were severe enough elevations to be reported to the FDA as SAEs. One of these seven subjects had been receiving a dose of 25 mg CDB-4124 per day; the remaining six subjects had been receiving a dose of 50 mg CDB-4124 per day. Liver enzymes ≥3×ULN persisted in five of the nine subjects with a confirmed increase in liver enzymes ≥3×ULN. These five subjects had previously been dosed with the 50 mg dose. One of these subjects is receiving oral medication for treatment of her liver condition. Clinical trials involving CDB-4124 at all doses were voluntarily suspended as a result of these SAEs and were subsequently placed on clinical hold by the United States Food and Drug Administration for safety reasons.

Pharmacokinetic studies performed on participating subjects detected a high $C_{max}$ and a $T_{max}$ at 1-2 hours following administration. Large quantities of the monodemethylated metabolite of CDB-4124 were also detected, clearly indicating first pass metabolism of the antiprogestin. Providing further evidence of first pass metabolism, primary cultures of human and animal hepatocytes rapidly produce the monodemethylated metabolite of CDB-4124. Metabolism of CDB-4124 by the liver provides the opportunity for liver damage and greatly reduces the concentration of the antiprogestin before it reaches the systemic circulation. Thus, alternative routes of administration of antiprogestins that avoid first pass metabolism such as, without limitation, intravenous, intramuscular, and sublingual, should allow antiprogestins to be absorbed directly into the systemic circulation and thereby provide a method for treating progesterone-dependent conditions while avoiding liver toxicity. Administration routes which avoid first pass metabolism may also require less drug per dose to achieve the same therapeutic benefit relative to oral administration.

Pre-clinical studies were performed on rodents with breast tumors induced by 7,12-Dimethylbenz(a)anthracene (DMBA). These studies demonstrated efficacy of non-oral delivery methods of CDB-4124. In particular, CDB-4124 delivered by subcutaneous injection was effective in reducing the quantity and size of DMBA-induced breast tumors providing proof of concept.

Example 4

Vaginal Delivery of CDB-4124 and CDB-4453 Reduces Systemic Concentrations Compared to Oral Administration and Avoids First Pass Metabolism Beagles were administered 25 mg of CDB-4124 or CDB-4453 (the monodemethylated metabolite of CDB-4124) formulated as either a micronized powder or a vaginal suppository. As illustrated at FIG. 1, CDB-4124 and CDB-4453, when administered orally as a micronized powder, are rapidly metabolized after a peak plasma concentration (Cmax) is achieved. In contrast, when the same compounds are administered locally via vaginal suppository, the drugs are metabolized slowly and peak plasma concentrations (Cmax) are relatively low. Moreover, systemic exposure of the drug is much lower when administered locally (compare AUC for CDB-4124 and CDB-4453 when administered vaginally vs. orally).

Figure 2:
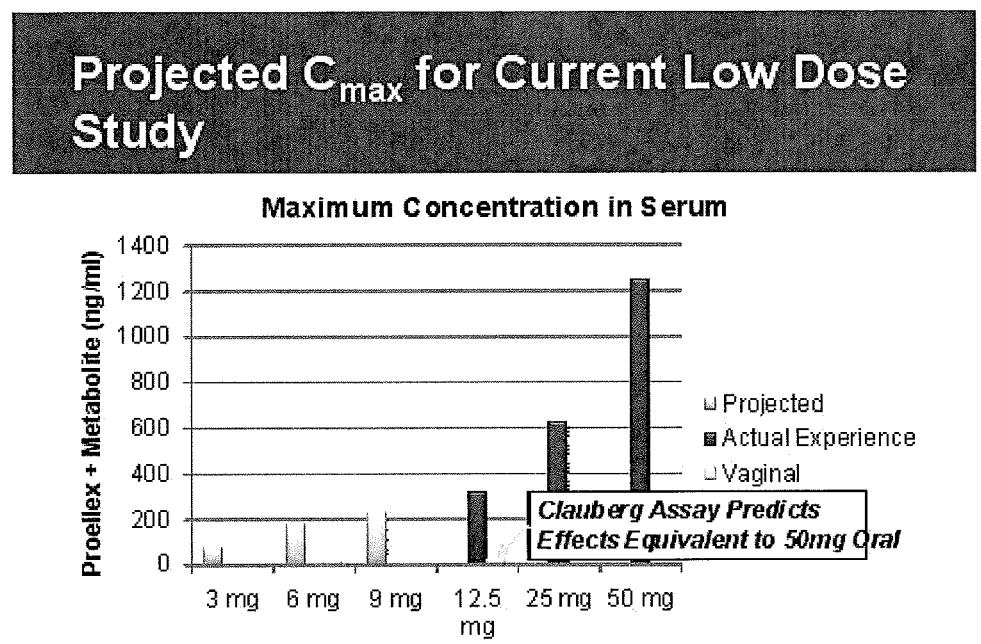
FIG. 2 illustrates the actual Cmax observed for Proellex (CDB-4124) and its monodemethylated metabolite CDB-4453, following oral administration of CDB-4124 at 12.5 mg, 25 mg and 50 mg doses as well as the projected Cmax for 3 mg, 6 mg and 9 mg doses.

The maximum circulating concentrations (Cmax) of CDB-4124 obtained following vaginal administration to beagles were extrapolated to humans for the 12.5 mg, 25 mg and 50 mg doses actually administered during the Phase III clinical studies. As can be seen from FIG. 2, the predicted Cmax for vaginal administration of the 12.5 mg dose of CDB-4124 in humans is approximately 6.5% of the same dose when administered orally and the predicted Cmax for vaginal administration of the 50 mg dose of CDB-4124 in humans is approximately 2% of the same dose when administered orally.

Example 5

Figure 3:
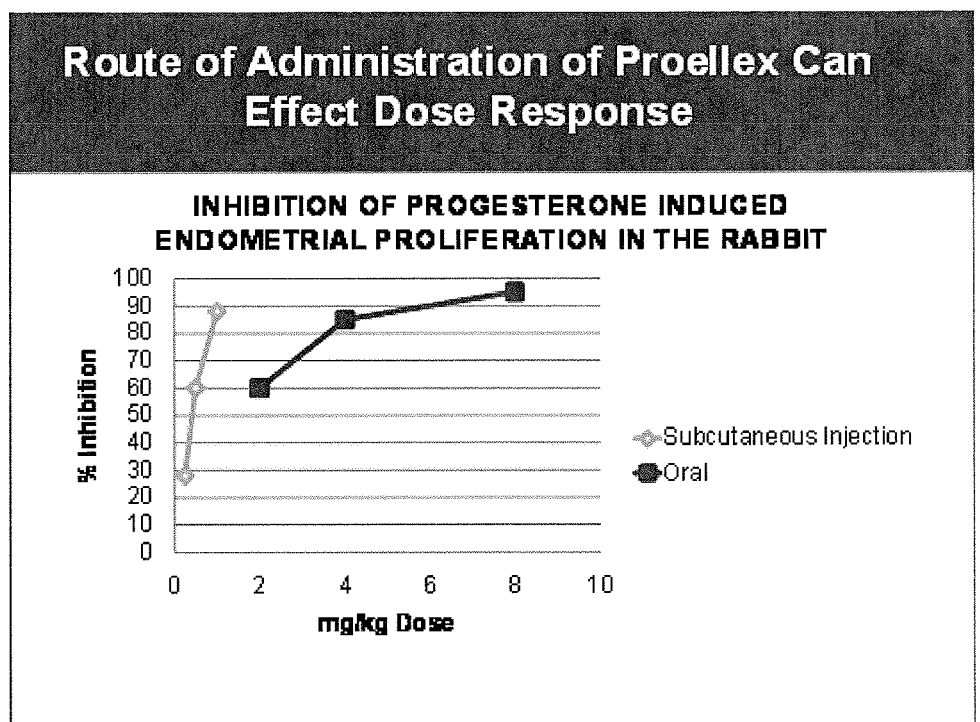
FIG. 3 illustrates a comparison of the inhibition of progesterone-induced endometrial proliferation in estradiol-primed immature rabbits following subcutaneous injection and oral administration of CDB-4124.
Figure 4:
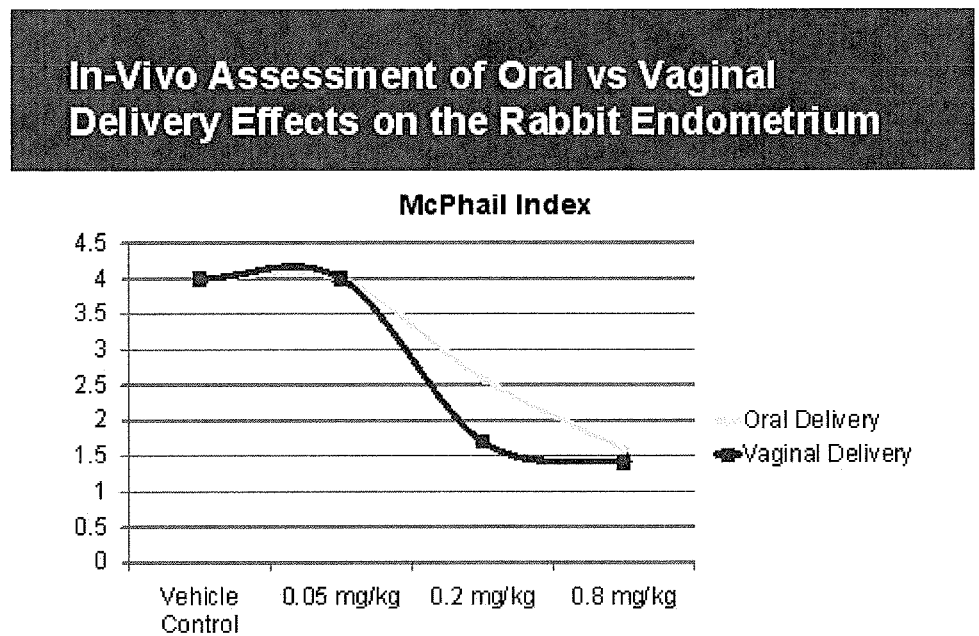
FIG. 4 compares the antiprogestational effects of three doses of CDB-4124 when delivered orally versus when delivered to the vaginal mucosa of estradiol-primed immature rabbits in the presence of progesterone, as measured by a decrease in the McPhail index. Treatment with progesterone alone (vehicle control) provided a baseline measurement of progestational activity.

Bioavailability of CDB-4124 at the Uterus is Surprisingly Low when Administered Orally To determine whether the low circulating levels of CDB-4124 when administered locally could have any impact predictive of efficacy, an anti-Clauberg study was run in which immature estradiol-primed rabbits were coadministered progesterone and various doses of CDB-4124 by either subcutaneous or oral administration. At least 3 different highly trained individuals evaluated the rabbit uterus for glandular growth, for complexity and overall progesterone-induced "development". The inhibition (by percentage) of progesterone-induced endometrial proliferation at each dose was assayed. As illustrated at FIG. 3, maximal inhibition was observed at a dose of less than 1 mg/kg when CDB-4124 was administered subcutaneously. However, maximal inhibition required a ~8-fold increase in dosage when administered orally (i.e. 8 mg/kg). Importantly 8 mg/kg corresponds closely to the 50 mg/day dose of CDB-4124 administered to the female subjects described in Example 3. This demonstrates that the effective local concentration of CDB-4124 at the endometrium is greatly decreased when the drug is administered orally, most likely due to first-pass metabolism of the drug. Accordingly, in order to achieve therapeutic effect, e.g. for indications localized to the pelvic and reproductive tract, a relatively high dosage of CDB-4124 is required when administered orally, corresponding closely to the dosage of CDB-4124 at which toxic liver effects were observed in Example 3.

Another anti-Clauberg study was run in which immature estradiol-primed rabbits were administered progesterone alone (vehicle control) or were coadministered progesterone and three doses of CDB-4124 by either vaginal or oral administration. The inhibition of progesterone-induced endometrial proliferation at each dose was assayed. FIG. 3 illustrates the decrease in the McPhail index following increasing doses of CDB-4124 administered by either route. Maximal inhibition (i.e. a decrease in the McPhail index to 1.5) occurred at 0.2 mg/kg CDB-4124 when administered vaginally, compared to 0.8 mg/kg when administered orally. The data from this study show that vaginal delivery of CDB-4124 exhibits four times the antiprogestational activity of the same oral dose.

Cumulatively, the data indicate that a four-fold lower dose of antiprogestin can be administered vaginally compared to the effective dose when orally administered, while attaining only a small fraction of the maximal circulating concentrations compared to oral administration, thereby avoiding liver toxicity. For example, equivalent antiprogestational activity at the uterus is observed for a 50 mg oral dose of CDB-4124 and a 12.5 mg vaginal dose; however, the Cmax observed with a 12.5 mg vaginal dose is only 2% that observed with a 50 mg oral dose. The relatively high local concentration of the drug achieved by local administration allows a relatively low dose of the drug (compared with oral administration) to achieve therapeutic effect for indications localized to the pelvic and reproductive tract (e.g. endometriosis, uterine fibroids and ovarian cancer). Because a high concentration of the drug in the systemic circulation (and associated first pass metabolism of the drug) is not reached by local administration, avoidance of the severe liver toxicity observed in a small percentage of subjects following oral administration of CDB-4124 in previous Phase III clinical studies at doses of 25 and 50 mg is a surprising advantage of administering the drug locally. Similar advantages should inure to local administration of other antiprogestins.

Example 6

Vaginal Administration of CDB-4124 for the Treatment of Uterine Fibroids

Seven human females with uterine fibroids have completed 4 months of treatment as part of a single blind study. These females were vaginally administered a daily dose of 12 mg CDB-4124 for a period of four months, with dosing initiated during the luteal phase of the females' menstrual cycles. At the end of the four month treatment period, all seven females stopped menstruating and all reported a Pictural Blood Loss Assessment Chart (PBAC) score of 0 (p=0.002). A statistically significant and highly clinically meaningful reduction in Uterine Fibroid Symptom Quality of Life Survey (UFSQOL) scores was also observed. The mean UFSQOL score at baseline was 43.8 and at the end of the four month treatment period the mean score was 1.33 (p=0.001). Both bleeding and bulk related symptoms assessed by the UFSQOL were dramatically reduced with six of the seven females responding that they no longer experienced any fibroid related symptoms. As a reference, women with fibroids typically score 40 or higher, whereas women without fibroids report scores of approximately 20.

Change in fibroid volume at the end of the four month treatment period determined by magnetic resonance imagining (MRI) was assessed and a statistically significant (chi square analysis) median reduction of total fibroid volume of 36% was observed.

In an oral study, doses of 1, 3, 6, 9 and 12 mg of CDB-4124 were administered for a period of 10 weeks. In the oral study, all doses were well tolerated and reliable cessation of menses was induced at doses as low as 3 mg. Cessation of menses directly correlated to efficacy of an oral dose in both uterine fibroids and endometriosis. Pharmacokinetic analysis revealed that vaginal administration of 12 mg of CDB-4124 resulted in about ⅙th the systemic exposure of an equivalent oral dose based on area under the curve (AUC) and a maximum exposure ($C_{max}$) about 1/100th of a 50 mg oral dose.

The concentration of CDB-4124 was observed to build slowly when the drug is vaginally administered relative to oral administration. Thus, the onset of amenorrhea is delayed when the drug is administered vaginally, necessitating that the drug be vaginally administered during subsequent menstruations, which tends to reduce absorption of the drug and is unpleasant and technically challenging for the patient. The methods of the present invention provide a solution to this problem by providing a brief period of oral administration, preceding and overlapping vaginal administration, which expedites the onset of amenorrhea while retaining the benefits of vaginal administration.

What is claimed is:

1. A method for treating a progesterone-dependent condition selected from the group consisting of endometriosis and pain associated therewith, adenomyosis, endometriomas of the ovary, dysmenorrhea, uterine fibroids, endometrial hyperproliferation, ovarian cancer, and cervical cancer in a female in need of such treatment comprising:

(a) orally administering a composition comprising a selective progesterone receptor modulator (SPRM) to the female daily for a period beginning on day 16 to 28 of a first menstrual cycle and ending on day 11-25 of a subsequent second menstrual cycle; and (b) contemporaneously vaginally administering a composition comprising an SPRM to the female daily for period beginning on day 1-10 of the second menstrual cycle and continuing until a desired therapeutic effect is achieved.

2. The method of claim 1, wherein the orally administered and vaginally administered SPRMs are the same.

3. The method of claim 2 wherein the SPRM is CDB-4124.

4. The method of claim 1 wherein the SPRM is orally administered at a dose of from 3 mg to 30 mg.

5. The method of claim 1 wherein the SPRM is vaginally administered at a dose of from 3 mg to 30 mg.

6. The method of claim 1 wherein the orally administered composition is a tablet or capsule.

7. The method of claim 1 wherein the vaginally administered composition comprises a bioadhesive carrier.

8. The method of claim 1 wherein the SPRM is vaginally administered at a dose of 3, 6, 12 or 24 mg.

9. The method of claim 8 wherein the SPRM is vaginally administered at a dose of 12 mg.

10. The method of claim 1 wherein the SPRM is orally administered at a dose of 3, 6, 12, or 24 mg.

11. The method of claim 1 wherein the progesterone-dependent condition is uterine fibroids or endometriosis.

12. The method of claim 1 wherein the vaginal administration is intermittent.

13. The method of claim 12 wherein the composition is administered vaginally on a daily basis consecutively over a period of about four months followed by a discontinuation period of sufficient length to allow the female to menstruate by means of a continual lack of treatment, after which the composition is administered on a daily basis for period of about four months, followed by a discontinuation period of sufficient length to allow the female to menstruate, after which the composition is administered on a daily basis and repeating this pattern of administration and discontinuance of administration for as long as necessary to achieve treatment of the progesterone-related condition.

14. A method for preventing or treating breast cancer in a female in need of such treatment comprising:

(a) orally administering a composition comprising a selective progesterone receptor modulator (SPRM) daily to the female; and (b) contemporaneously transdermally administering a composition comprising an SPRM to the female daily until a desired therapeutic effect is achieved.

15. The method of claim 14, wherein the orally administered and transdermally administered SPRMs are the same.

16. The method of claim 15 wherein the SPRM is CDB-4124.

17. The method of claim 14 wherein the SPRM is orally administered and/or transdermally administered at a dose of from 3 mg to 30 mg.

18. The method of claim 14 wherein oral administration is co-extensive with transdermal administration.

* * * * *